US012582370B2

(12) United States Patent
Manjunath et al.

(10) Patent No.: US 12,582,370 B2
(45) Date of Patent: Mar. 24, 2026

(54) SYSTEM AND METHOD FOR DETERMINING HIGH-TEMPERATURE REGION PIXELS ON A MAMMOGRAPHY IMAGE

(71) Applicant: Niramai Health Analytix Pvt. Ltd., Bangalore (IN)

(72) Inventors: Geetha Manjunath, Bangalore (IN); Siva Teja Kakileti, Kakinada (IN); Minerva Panda, Bhubaneswar (IN); Sudhakar Sampangi, Kolar (IN)

(73) Assignee: NIRAMAI HEALTH ANALYTIX PVT. LTD, Bangalore (IN)

( * ) Notice: Subject to any disclaimer, the term of this patent is extended or adjusted under 35 U.S.C. 154(b) by 188 days.

(21) Appl. No.: 18/696,949

(22) PCT Filed: Sep. 22, 2022

(86) PCT No.: PCT/IN2022/050846
§ 371 (c)(1),
(2) Date: Mar. 28, 2024

(87) PCT Pub. No.: WO2023/053133
PCT Pub. Date: Apr. 6, 2023

(65) Prior Publication Data
US 2024/0415477 A1      Dec. 19, 2024

(30) Foreign Application Priority Data
Sep. 29, 2021    (IN) .............................. 202141044322

(51) Int. Cl.
*A61B 6/50* (2024.01)
*G16H 30/40* (2018.01)

(52) U.S. Cl.
CPC ............. *A61B 6/502* (2013.01); *G16H 30/40* (2018.01)

(58) Field of Classification Search
CPC ..... A61B 6/502; A61B 6/0414; A61B 6/5294; A61B 6/032; A61B 5/0035; A61B 5/015;
(Continued)

(56) References Cited

U.S. PATENT DOCUMENTS

| 12,039,725 | B2 * | 7/2024 | Panda | ................... | G06T 7/0012 |
| 12,324,680 | B1 * | 6/2025 | Lochner | ................. | A61B 5/444 |

(Continued)

*Primary Examiner* — Casey Bryant

(57) ABSTRACT

A system for annotating mammography images of a subject using thermal images and mammography images of the subject using thermal and mammography images of the subject by (i) identifying a first breast region in the thermal image and a second breast region in the mammography image, (ii) identifying a block of pixels $(P_t)$ with a high temperature region associated with a breast lesion within the first breast region, (iii) estimating a location (l) of the breast lesion corresponding to the identified block of pixels $(P_t)$, (iv) determining a block of pixels $(P_m)$ corresponding to the location (l) of the block of pixels $(P_t)$ within the second breast region and (v) generating a report with an annotated mammography image with markings of a determined block of pixels $(P_m)$ on the mammography image of the subject corresponding to the block of pixels $(P_t)$ on the thermal image.

20 Claims, 13 Drawing Sheets

(58) Field of Classification Search
CPC .... A61B 5/4312; A61B 5/7267; A61B 5/7485
See application file for complete search history.

(56) References Cited

U.S. PATENT DOCUMENTS

| | | | |
|---|---|---|---|
| 12,343,116 B2 * | 7/2025 | Kakileti | ................. A61B 5/004 |
| 2006/0004278 A1 * | 1/2006 | Giger | ........................ G06T 7/35 |
| | | | 600/408 |
| 2018/0000461 A1 * | 1/2018 | Venkataramani | .... A61B 5/4312 |

\* cited by examiner

502

502

704

704

708

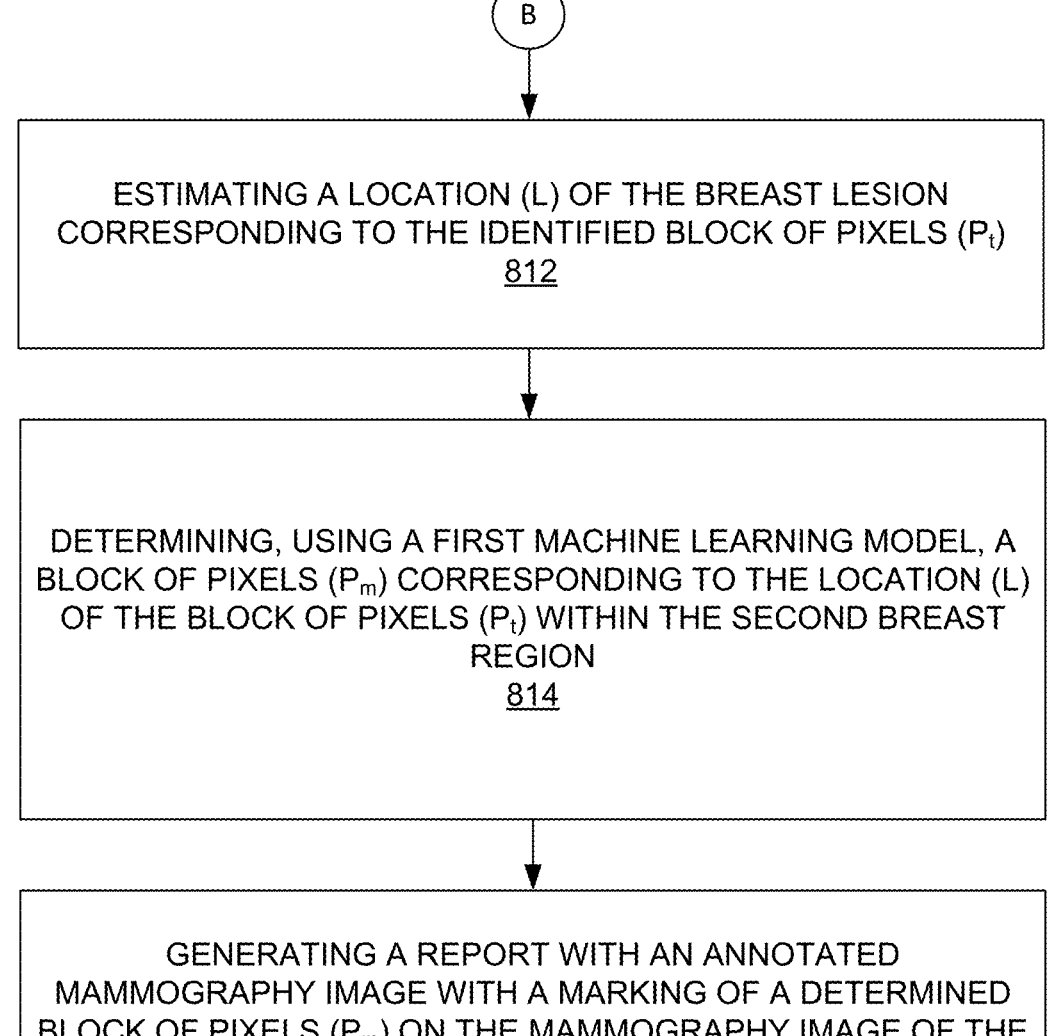

ESTIMATING A LOCATION (L) OF THE BREAST LESION CORRESPONDING TO THE IDENTIFIED BLOCK OF PIXELS ($P_t$)
812

DETERMINING, USING A FIRST MACHINE LEARNING MODEL, A BLOCK OF PIXELS ($P_m$) CORRESPONDING TO THE LOCATION (L) OF THE BLOCK OF PIXELS ($P_t$) WITHIN THE SECOND BREAST REGION
814

GENERATING A REPORT WITH AN ANNOTATED MAMMOGRAPHY IMAGE WITH A MARKING OF A DETERMINED BLOCK OF PIXELS ($P_m$) ON THE MAMMOGRAPHY IMAGE OF THE SUBJECT CORRESPONDING TO THE BLOCK OF PIXELS ($P_t$) ASSOCIATED WITH THE HIGH TEMPERATURE REGIONS ON THE THERMAL IMAGE TO ENABLE LESION IDENTIFICATION ON THE MAMMOGRAPHY IMAGE OF THE SUBJECT
816

FIG. 8B

SYSTEM AND METHOD FOR DETERMINING HIGH-TEMPERATURE REGION PIXELS ON A MAMMOGRAPHY IMAGE

TECHNICAL FIELD

The embodiments herein generally relate to thermography and mammography, more particularly, a system and method for annotating mammography images of a subject using thermal images and mammography images of the subject by determining a block of pixels on the mammography images corresponding to high temperature regions on the thermal images.

DESCRIPTION OF THE RELATED ART

In today's world, along with technological advances, diseases and illnesses of all types are growing as well. Cancer has cropped up as one such disease causing an alarming rate of deaths. The detection of cancer along with its severity is one of the major problems with a disease such as cancer. By the time the symptoms of cancer are realized, the severity of and spread would already reach a dire stage. Researchers across the world have identified breast cancer as the leading type of cancer that is widespread among women. Breast cancer ranks second among all cancers in respect to death rates worldwide. Survival rates are extremely low, especially in developing countries like India. Research shows high survival rates, improved quality of life, and cost-effective treatment for those whose breast cancer is detected at an early stage. Mammography is commonly used to examine human breasts for primary screening and diagnosis. Radiologists use mammographic images to detect breast cancer, as it is efficient in recording the visualized details of the internal regions of the breast. However, the accuracy of mammography images drops down drastically to about 50% for women with dense breasts, making the usage of mammography ineffective for young women. Further, the interpretation of mammography images requires high expertise. In developing countries like India, this becomes a major hurdle due to the shortage of experienced radiologists.

Thermography is an FDA-approved adjunct modality for breast cancer detection. Thermography captures the amount of heat radiating from the surface of the body and in particular, breast thermography measures the temperature patterns and thermal distribution on the chest due to the high metabolism associated with tumorous growth. There are several advantages to breast thermography compared to other breast imaging modalities. It is low-cost imaging, non-contact, works on women of all age groups, is irradiation-free, and privacy aware. This also makes it suitable for developing countries like India. Today, detecting early-stage breast cancer might not be possible with a single standalone test. Therefore, the use of breast thermography adjunct to mammography can help in improving the detection of breast cancers. However, this requires a correlation of the high thermal regions on thermal images to the high-density region on the mammography images. This is not a trivial problem as the reference systems of mammography imaging and thermal imaging are different. Mammography captures the cross-section density information of the breast, whereas thermography captures surface temperature distribution.

Therefore, there arises a need to address the aforementioned technical drawbacks in existing technologies to determine an overlapping lesion region of a thermal image on a mammography image.

SUMMARY

In view of foregoing an embodiment herein provides a system for annotating mammography images of a subject using thermal images and mammography images of the subject by determining a block of pixels on the mammography images corresponding to high temperature regions on the thermal images. The system includes a thermal imaging device, a mammography imaging device, and a processor. The thermal imaging device captures a thermal image of the subject. The mammography imaging device captures the mammography image of the subject. The processor is configured to (i) identify a first breast region in the thermal image of the subject, (ii) identify a second breast region in the mammography image of the subject, (iii) identify a block of pixels ($P_t$) with the high temperature region associated with a breast lesion within the first identified breast region, (iv) estimates a location (l) of the breast lesion corresponding to the identified block of pixels ($P_t$), (v) determine, using a first machine learning model, a block of pixels ($P_m$) on the mammography image corresponding to the location (l) of the block of pixels ($P_t$) within the second breast region and (vi) generate a report with an annotated mammography image with a marking of a determined block of pixels ($P_m$) on the mammography image of the subject corresponding to the block of pixels ($P_t$) associated with the high temperature regions on the thermal image to enable lesion identification on the mammography image of the subject.

In some embodiments, the thermal imaging device includes an array of sensors and a specialized thermal processor. The array of sensors converts infrared energy into electrical signals on a per-pixel basis. The array of sensors detects temperature values from the subject. The specialized thermal processor processes detected temperature values into pixels of a thermal image. The intensity values of the pixels correspond to the detected temperature values.

In some embodiments, the mammography imaging device includes an X-ray tube, a plurality of filters, a plurality of compression paddles, and a specialized mammogram processor. The X-ray tube produces low energy X-rays. The plurality of filters is placed in a path of X-ray beam to modify an X-ray spectrum that is projected on the body of the subject. The plurality of compression paddles attached to the body of the subject to compress a part of the body of the subject being exposed to the X-rays to obtain cross-section density information. The specialized mammogram processor converts obtained cross-section density information into pixels to generate a mammography image. The intensity values of the pixels correspond to the obtained cross-section density information on at per-pixel basis.

In some embodiments, the processor is configured to identify the block of pixels ($P_t$) with high-temperature regions on the thermal image of the breast region of the subject by determining a first pixel region ($m_1$) with a temperature $T_{pixel}$, where $T_2 \le T_{pixel} \le T_1$. The $T_1$, and $T_2$ are temperature thresholds obtained from a temperature distribution.

In some embodiments, the processor is configured to identify the block of pixels ($P_t$) with the high temperature regions on the thermal image of the breast region of the subject by (i) determining the first pixel region ($m_1$) with a temperature $T^1_{pixel}$, where $T_2 \le T^1_{pixel} \le T_1$, (ii) determining a second pixel region ($m_2$) with a temperature $T^2_{pixel}$, where $T_3 \leq T^2_{pixel}$, and (iii) detecting a plurality of hotspot regions using the first pixel region ($m_1$) and the second pixel region ($m_2$) with AND or OR rules. The $T_1$, $T_2$ and $T_3$ are temperature thresholds obtained from a temperature distribution.

In some embodiments, the processor is configured to obtain the plurality of high temperature regions on the first breast region of the subject as an input from the user to estimate the location (l) of the breast lesion corresponding to the block of pixels ($P_t$) in the thermal image of the subject.

In some embodiments, the processor is configured to identify the block of pixels ($P_t$) with high temperature regions on the first breast region of the subject using a second machine learning model. The second machine learning model is trained by providing a plurality of thermal images and corresponding annotated high temperature regions associated with different patients as training data. In some embodiments, the first machine learning model identifies the block of pixels ($P_m$) on the mammography image corresponding to the location (l) on the thermography image by (i) obtaining a breast quadrant corresponding to the location (l), (ii) identifying a view of the mammography image, (iii) dividing the mammography image into different quadrants and (iv) identifying the block of pixels ($P_m$) that lie within a obtained quadrant corresponding to location (l) of the breast lesion on the thermographic image In some embodiments, the first machine learning model identifies the block of pixels ($P_m$) on the mammography image corresponding to the location (l) on the thermography image by (i) identify candidate block of pixels with high density in the mammography image, (ii) obtaining a nipple point (N) on the mammography image, (iii) calculating locations ($lm_{1-n}$) of each candidate block of pixels with respect to a obtained nipple point (N), (iv) comparing the locations ($lm_{1-n}$) of each of the candidate block of pixels with the location (l) of the breast lesion on the thermographic image and (v) selecting the block of pixels ($P_m$) among the candidate block of pixels by selecting a block of pixels corresponding to a nearest location ($lm_t$) among the locations ($lm_{1-n}$) that is close to the location (l) of the breast lesion on the thermographic image.

In some embodiments, the first machine learning model identifies the block of pixels ($P_m$) on the mammography image corresponding to the location (l) on the thermography image including (i) obtaining a clock position ($\theta$) and a distance (r) from the location (l), (ii) dividing the mammography image into different sectors corresponding to different clock positions and (iii) identifying the block of pixels ($P_m$) that lie within the sector corresponding to the clock position ($\theta$) and distance (r) from the nipple region in the mammography image.

In some embodiments, the processor is configured to identify the block of pixels ($P_m$) as the high-density regions in the mammography image within the sector corresponding to the clock position ($\theta$) and distance (r) from the nipple region in the mammography image.

In some embodiments, the processor is configured to identify the high-density regions on the mammography image of the subject using a third machine learning model. The third machine learning model is trained by providing a plurality of mammography images and the corresponding annotated high-density lesions associated with different patients as training data.

In some embodiments, the report includes at least one of (i) annotated mammography image with markings of the determined block of pixels ($P_m$) in a different color as annotations on the mammography image, (ii) annotated mammography image with markings of the boundary of the determined block of pixels ($P_m$) in a different color as annotations on the mammography image and (iii) a text report that includes quantitative parameters of the block of pixels ($P_m$) on the mammography image corresponding to the high temperature region on the thermal image.

In some embodiments, the markings include an annotation of the block of pixels ($P_m$) on the mammogram image corresponding to the high temperature region on the thermal image and a text annotation that includes quantitative parameters of the block of pixels ($P_m$).

In another aspect, a method for annotating mammography images of a subject using thermal images and mammography images of the subject by determining a block of pixels on the mammography images corresponding to high temperature regions on the thermal images including (i) capturing a thermal image of the subject using a thermal imaging device, (ii) capturing the mammography image of the subject using a mammography imaging device, (iii) identifying a first breast region in the thermal image of the subject, (iv) identifying a second breast region in the mammography image of the subject, (v) identifying a block of pixels ($P_t$) with the high temperature region associated with a breast lesion within the first identified breast region, (vi) estimating a location (l) of the breast lesion corresponding to the identified block of pixels ($P_t$), (vii) determining, using a first machine learning model, a block of pixels ($P_m$) on the mammography image corresponding to the location (l) of the block of pixels ($P_t$) within the second breast region and (viii) generating a report with an annotated mammography image with a marking of a determined block of pixels ($P_m$) on the mammography image of the subject corresponding to the block of pixels ($P_t$) associated with the high temperature regions on the thermal image to enable lesion identification on the mammography image of the subject.

The system and method allow the thermal image as an adjunct to mammography image in a completely automated method. This adjunctive-ness allows the physician to identify the high-density regions that include high thermal activities. This information is used for at least one diagnosis, prognosis, and treatment monitoring. The system and method include the adjunctive-ness that is used by a machine-learning algorithm to improve the overall accuracy of breast cancer detection.

These and other aspects of the embodiments herein will be better appreciated and understood when considered in conjunction with the following description and the accompanying drawings. It should be understood, however, that the following descriptions, while indicating preferred embodiments and numerous specific details thereof, are given by way of illustration and not of limitation. Many changes and modifications may be made within the scope of the embodiments herein without departing from the spirit thereof, and the embodiments herein include all such modifications.

BRIEF DESCRIPTION OF THE DRAWINGS

The embodiments herein will be better understood from the following detailed description with reference to the drawings, in which:

FIGS. 8A and 8B are flow diagrams that illustrate a method for annotating mammography images of a subject using thermal images and mammography images of the subject by determining a block of pixels on the mammography images corresponding to high temperature regions on the thermal images according to an embodiment herein.

DETAILED DESCRIPTION OF THE DRAWINGS

Figure 1:
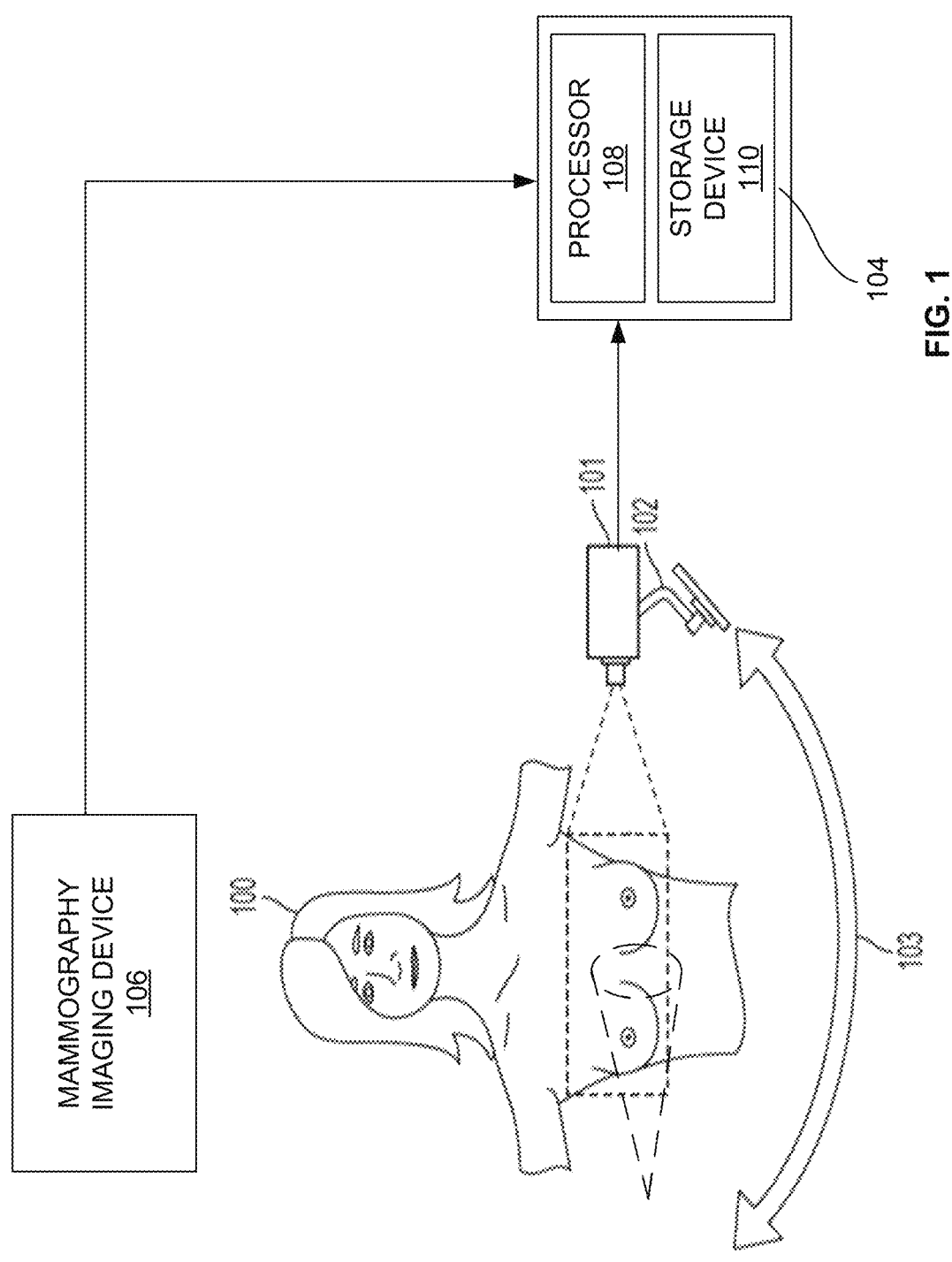
FIG. 1 illustrates a system view of annotating mammography images of a subject using thermal images and mammography images of the subject by determining a block of pixels on the mammography images corresponding to high temperature regions on the thermal images according to an embodiment herein.

The embodiments herein and the various features and advantageous details thereof are explained more fully with reference to the non-limiting embodiments that are illustrated in the accompanying drawings and detailed in the following description. Descriptions of well-known components and processing techniques are omitted so as to not unnecessarily obscure the embodiments herein. The examples used herein are intended merely to facilitate an understanding of ways in which the embodiments herein may be practiced and to further enable those of skill in the art to practice the embodiments herein. Accordingly, the examples should not be construed as limiting the scope of the embodiments herein.

As mentioned, there remains a need for a system and a method for determining a block of pixels corresponding to high temperature regions on a mammography image by annotating mammography images of a subject using thermal images and mammography images of the subject. Referring now to the drawings, and more particularly to FIGS. 1 through 10, where similar reference characters denote corresponding features consistently throughout the figures, there are shown preferred embodiments.

A "person" and "subject" refer to either a male or a female. Gender pronouns are not to be viewed as limiting the scope of the appended claims strictly to females. Moreover, although the terms "person", "patient" or "subject" are used interchangeably throughout this disclosure, it should be appreciated that the person undergoing breast cancer screening may be something other than a human such as, for example, a primate. Therefore, the use of such terms is not to be viewed as limiting the scope of the appended claims to humans.

A "breast area" refers to the tissue of the breast and may further include surrounding tissue as is deemed appropriate for breast cancer screening.

A "thermal camera" refers to either a still camera or a video camera with a lens that focuses infrared energy from objects in a scene onto an array of specialized sensors which convert infrared energy across a desired thermal wavelength band into electrical signals on a per-pixel basis and which output an array of pixels with colours that correspond to temperatures of the objects in the image.

A "thermographic image" or simply a "thermal image" is an image captured by a thermal camera. The thermographic image comprises an array of color pixels with each color being associated with temperature. Pixels with a higher temperature value are displayed in the thermal image in a first color and pixels with a lower temperature value are displayed in a second color. Pixels with temperature values between the lower and higher temperature values are displayed in gradations of color between the first and second colors.

A "mammography imaging device" generates the mammography image of the breast area of the subject. The breast area of the subject is placed on a flat support plate and compressed with a parallel plate called a paddle. The mammography imaging device produces a small burst of X-rays that pass through the breast area to a detector that is located on the opposite side. The detector captures the x-ray image on film, or a solid-state detector, which transmits electronic signals to a computer to form a mammography image.

A "mammography image" is an X-ray image of the breast area of the subject. The background of the mammography image is displayed in black and the breast is in grays and whites.

FIG. 1 illustrates a system view of annotating mammography images of a subject using thermal images and mammography images of the subject by determining a block of pixels on the mammography images corresponding to high temperature regions on the thermal images according to an embodiment herein. The system view includes a subject 100, a thermal imaging device 101, a computing system 104, and a mammography imaging device 106. The computing device 104 includes a processor 108 and a storage device 110. In one embodiment, the thermal imaging camera 101 is mounted on the slidable and an axially rotatable robotic arm that is capable of moving the thermal imaging camera 101 along a semi-circular trajectory 103 in the front of the patient/subject from side-to-side such that thermographic images may be captured in a right-side view, a front view, and a left-side view, and various oblique angles in between. In some embodiments, the thermographic images are captured in different views manually by moving the thermal imaging device 101 or subject by a user. In some embodiments, the thermographic images are captured using at least one of the thermal sensors or wearable devices. In some embodiments, the thermal imaging device 101 consists of an array of sensors and a specialized thermal processor. The array of sensors converts infrared energy into electrical signals on a per-pixel basis. The array of sensors in a thermal imaging device 101 detects temperature values from a body of the subject 100. The specialized thermal processor in the thermal imaging device 101 processes the detected temperature values into at least one block of pixels to generate a thermal image. In some embodiments, the thermal imaging device includes a first screen that shows the temperature values captured by the thermal imaging device 101, along with hotspots (high temperature regions) of the body of the subject 100. In some embodiments, the mammography imaging device 106 includes a second screen that shows information related to the mammography image of the subject 100. In some embodiments, the thermal image includes an upper body region of the subject's body. The mammography imaging device 106 captures a mammography image of the body of the subject 100 and generates standard views. In some embodiments, the standard views include, but are not limited to bilateral craniocaudal view and mediolateral oblique view. In some embodiments, the mammography imaging device 106 includes an X-ray tube, a plurality of filters, a plurality of compression paddles, and a specialized mammogram processor. The X-ray tube produces low energy X-rays. The plurality of filters is placed in the path of the X-ray beam to modify the x-ray spectrum that is projected on the body of the subject 100. The plurality of compression paddles is attached to the body of the subject 100 to compress apart of the body of the subject 100 being exposed to the X-rays to obtain cross section density information. The specialized mammogram processor converts obtained cross section density information into pixels to generate a mammography image. In some embodiments, intensity values of the pixels correspond to the obtained cross section density information on a per-pixel basis.

The storage device 110 stores a set of instructions that are executed by the processor 108 for performing one or more functions. A thermal image from the thermal imaging device 101 and a mammography image from the mammography imaging device 106 are received by the computing system 104 to determine the block pixels associated with the high-density region on a mammography image. In some embodiments, the thermal image and mammography image are provided to the computing system 104, using a wired network or a wireless network such as a Bluetooth, Wi-Fi, ZigBee, cloud, or any other communication network. In some embodiments, the thermal image and the mammography image contain one or more features such as a user ID, a timestamp, user interaction details, a number of distinct applications launched by the thermal imaging device 101 or mammography imaging device 106. In some embodiments, the computing system 104 obtains functional and structural images from a Compact Disc Read-Only Memory (CDROM) or Digital Versatile/Video Disc (DVD). The functional and structural images may be downloaded from a web-based system or an application that makes the thermal and mammography images available for processing. In some embodiments, the thermal images and mammography images are received from a mobile application that is available on a handheld device. In some embodiments, the handheld device includes but is not limited to, a cell phone, a handheld computing device, an electronic notepad, a smart phone, and a personal assistant device. In some embodiments, the thermal images and mammography images are received directly from a memory or the storage device 110 of the computing system 104. The storage device 110 stores the data received from the thermal imaging device 101 and the mammography imaging device 106 as an input file along with data processed by the processor 108. In some embodiments, the input file may be one or more two-dimensional images produced by the thermal imaging device 101 and the mammography imaging device 106, being stored in the data storage in a digital imaging and communications in medicine (DICOM) format. In some embodiments, the thermal imaging device 101 and mammography imaging device 106 may collect data of the subject 100 in the DICOM format. In some embodiments, the computing system 104 may use the input file data of the subject 100 in the DICOM format, for example, the data of the subject 100 may include a number of attributes such as a name of the subject 100, an ID of the subject 100, medical history of the subject 100, a number of slices of the thermal and mammography images, a voxel size, a number of functional time-series points from a DICOM header for image processing.

The computing device 104 identifies the block of pixels $(P_t)$ with the high temperature associated with a breast lesion within an identified first breast region of the thermal image. The computing device 104 estimates the location (l) of the breast lesion corresponding to the block of pixels $(P_t)$ in the thermal image. The computing device 104 determines a block of pixels $(P_m)$ on the mammography image corresponding to the location (l) of the block of pixels $(P_t)$ within the second breast region using a first machine learning model. The computing device 104 generates a report with an annotated mammography image with a marking of a determined block of pixels $(P_m)$ on the mammography image of the subject 100 corresponding to the block of pixels $(P_t)$ associated with the high temperature regions on the thermal image to enable lesion identification on the mammography image of the subject 100.

Figure 2:
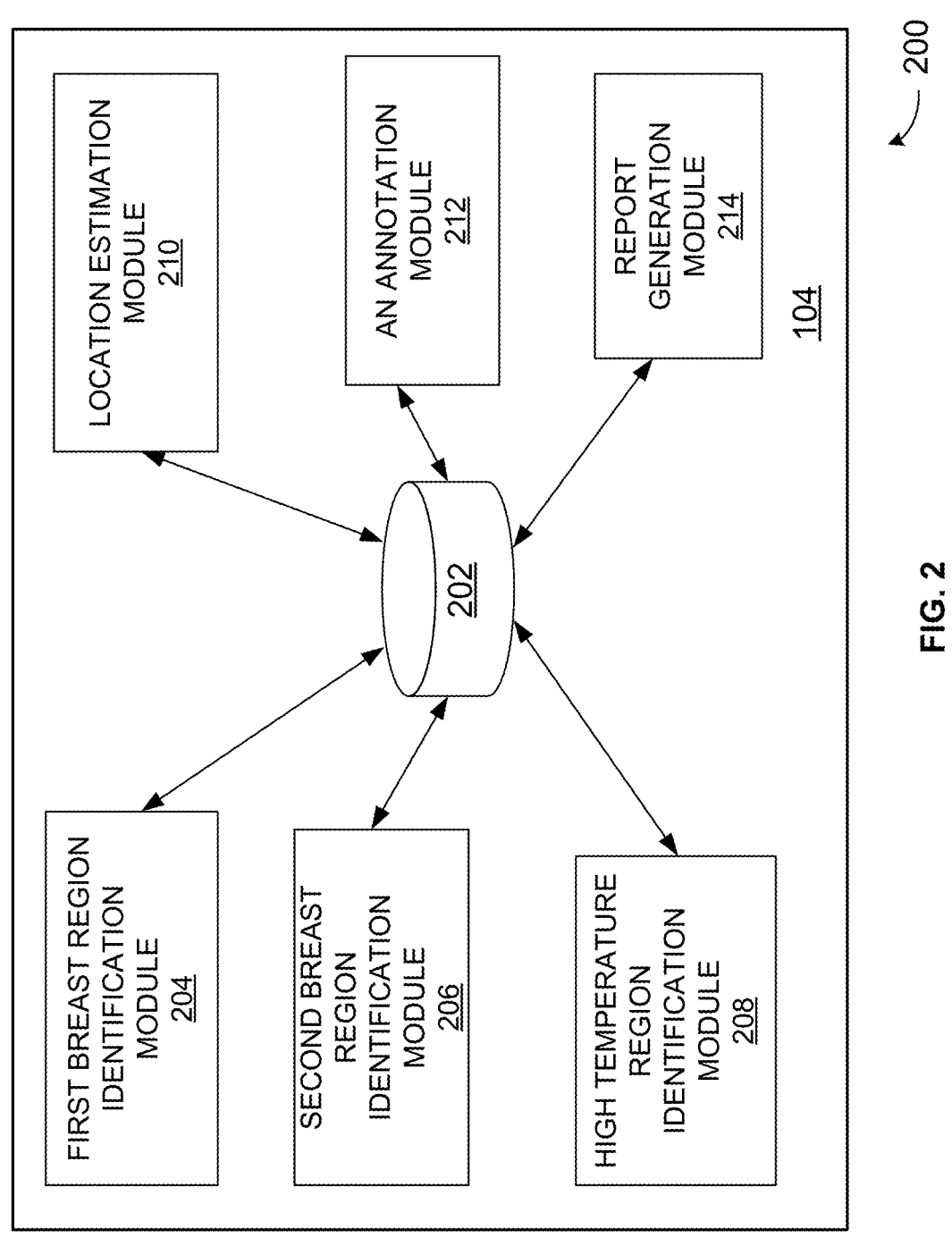
FIG. 2 illustrates an exploded view of the computing system 104 according to an embodiment herein.

With reference to FIG. 1, FIG. 2 illustrates an exploded view of the computing system 104 according to an embodiment herein. The computing system 104 includes a database 202, a first breast region identification module 204, a second breast region identification module 206, a high temperature region identification module 208, a location estimation module 210, an annotation module 212, and a report generation module 214. The database 202 stores thermal images and mammography images that are received from the thermal imaging device 101 and the mammography imaging device 106. In some embodiments, the thermal images and the mammography images are stored in a DICOM format. The DICOM format includes data sets with a header and imagery data set, not limited to the thermal images, the mammography images. In some embodiments, the thermal images and the mammography images of the subject may include one or more attributes (for example, a name of the subject, an identification (ID) of the subject, etc.), a number of slices of the images, a voxel size, and a number of functional time-series points from a DICOM header. In some embodiments, the thermal images and the mammography images are pre-processed to improve the image quality to precisely distinguish between defected and non-defected images.

The first breast region identification module 204, identifies a first breast region on the thermal image of the subject 100. In some embodiments, the first breast region identification module 204 obtains the thermal image from the thermal imaging device 101 and identifies the first breast region using machine learning models. In some embodiments, the first breast region is identified on the thermal image of the subject 100 manually. The second breast region identification module 206 identifies a second breast region on the mammography image of the subject 100. In some embodiments, the second breast region identification module 206 obtains the mammography image from the mammography imaging device 106 and identifies the second breast region using machine learning models. In some embodiments, the second breast region is identified on the mammography image of the subject 100 manually.

The high temperature region identification module 208 identifies a block of pixels ($P_t$) with a high temperature region associated with a breast lesion within the first identified breast region. The block of pixels ($P_t$) with the high temperature regions is identified on the thermal image of the breast region of the subject by determining a first pixel region ($m_1$) with a temperature $T_{pixel}$, where $T_2 \leq T_{pixel} \leq T_1$, wherein $T_1$, and $T_2$ are temperature thresholds obtained from a temperature distribution. The block of pixels ($P_t$) with the high temperature regions is identified on the thermal image of the breast region of the subject by (i) determining the first pixel region ($m_1$) with a temperature $T^1_{pixel}$, where $T_2 \leq T^1_{pixel} \leq T_1$, (ii) determining a second pixel region ($m_2$) with a temperature $T^2_{pixel}$, where $T_3 \leq T^2_{pixel}$ and (iii) detecting a plurality of hotspot regions using the first pixel region ($m_1$) and the second pixel region ($m_2$) with AND or OR rules. The $T_1$, $T_2$, and $T_3$ are temperature thresholds obtained from a temperature distribution. The block of pixels ($P_t$) with the high temperature regions is identified on the first breast region of the subject using a second machine learning model. The second machine learning model is trained by providing a plurality of thermal images and corresponding annotated high temperature regions associated with different patients as training data. In some embodiments, the $T_1$ may be a maximum temperature and $T_2$ is calculated from a histogram of the breast thermal image. In some embodiments, $T_1$, $T_2$, and $T_3$ are provided by a user.

The location estimation module 210 estimates a location (l) of the breast lesion corresponding to the identified block of pixels ($P_t$). In some embodiments, the plurality of high temperature regions on the first breast region of the subject is obtained as an input from a user to estimate the location (l) of the breast lesion corresponding to the block of pixels ($P_t$) in the thermal image of the subject 100. The first location (l) of pixels associated with the high temperature regions is obtained as a plurality of two-dimensional coordinates by considering a two-dimensional coordinate system with a nipple as an origin and a breast region as the boundary.

The annotation module 212 determines a block of pixels ($P_m$) on the mammography image corresponding to the location (l) of the block of pixels ($P_t$) within the second breast region using a first machine learning model. The first machine learning model identifies the block of pixels ($P_m$) on the mammography image corresponding to the location (l) on the thermography image by (i) obtaining a clock position ($\theta$) and a distance (r) from the location (l), (ii) dividing the mammography image into different sectors corresponding to different clock positions, and (iii) identifying the block of pixels ($P_m$) that lies within a sector corresponding to the clock position ($\theta$) and at a minimum distance (r) from a nipple region in the mammography image. In some embodiments, the block of pixels ($P_m$) is identified as the high-density regions in the mammography image within the sector corresponding to the clock position ($\theta$) and at a minimum distance (r) from the nipple region in the mammography image. In some embodiments, the high-density regions are identified on the mammography image of the subject 100 using a third machine learning model. The third machine learning model is trained by providing a plurality of mammography images and the corresponding annotated high-density lesions associated with different patients as training data.

In some embodiments, the first machine learning model identifies the block of pixels ($P_m$) on the mammography image corresponding to the location (l) on the thermography image by (i) obtaining a breast quadrant corresponding to the location (l), (ii) identifying a view of the mammography image, (iii) dividing the mammography image into different quadrants and (iv) identifying the block of pixels ($P_m$) that lie within a obtained quadrant corresponding to location (l) of the breast lesion on the thermographic image In some embodiments, the first machine learning model identifies the block of pixels ($P_m$) on the mammography image corresponding to the location (l) on the thermography image by (i) identify candidate block of pixels with high density in the mammography image, (ii) obtaining a nipple point (N) on the mammography image, (iii) calculating locations ($lm_{1-n}$) of each candidate block of pixels with respect to a obtained nipple point (N), (iv) comparing the locations ($lm_{1-n}$) of each of the candidate block of pixels with the location (l) of the breast lesion on the thermographic image and (v) selecting the block of pixels ($P_m$) among the candidate block of pixels by selecting a block of pixels corresponding to a nearest location ($lm_i$) among the locations ($lm_{1-n}$) that is close to the location (l) of the breast lesion on the thermographic image. In some embodiments, the location of the candidate block of pixels with the location (l) of the breast lesion on the thermographic image includes $lm_1$, $lm_2$ to $lm_{m-n}$.

The report generation module 214 generates a report with an annotated mammography image with a marking of a determined block of pixels ($P_m$) on the mammography image of the subject corresponding to the block of pixels ($P_t$) associated with the high temperature regions on the thermal image to enable lesion identification on the mammography image of the subject. The report includes at least one of (i) annotated mammography image with markings of the determined block of pixels ($P_m$) in a different color as annotations on the mammography image, (ii) annotated mammography image with markings of the boundary of the determined block of pixels ($P_m$) in a different color as annotations on the mammography image and (iii) a text report that includes quantitative parameters of the block of pixels ($P_m$) on the mammography image corresponding to the high temperature region on the thermal image. The markings include an annotation of the block of pixels ($P_m$) on the mammogram image corresponding to the high temperature region on the thermal image and a text annotation that comprises quantitative parameters of the block of pixels ($P_m$). In some embodiments, the first machine learning model, the second machine learning model, and the third machine learning model include supervised learning algorithms and unsupervised learning algorithms. In some embodiments, the supervised learning algorithms include a decision tree learning, a linear model analysis, a support vector machine algorithm, graphical models, deep neural networks, an ensemble learning algorithm, classification models, and regression models. In some embodiments, the unsupervised learning algorithms include a clustering-based algorithm, a graph-based algorithm, a component-based learning algorithm, a hierarchical clustering-based algorithm, deep neural networks, and a mixture model. In some embodiments, the markings may be displayed on a DICOM overlaying on the actual mammogram image or a mammogram image with a high density making represented in a different color. In some embodiments, the markings are test annotations on the DICOM or a text report characteristic of lesions corresponding to the high temperature regions.

Figures 3A, 3B:
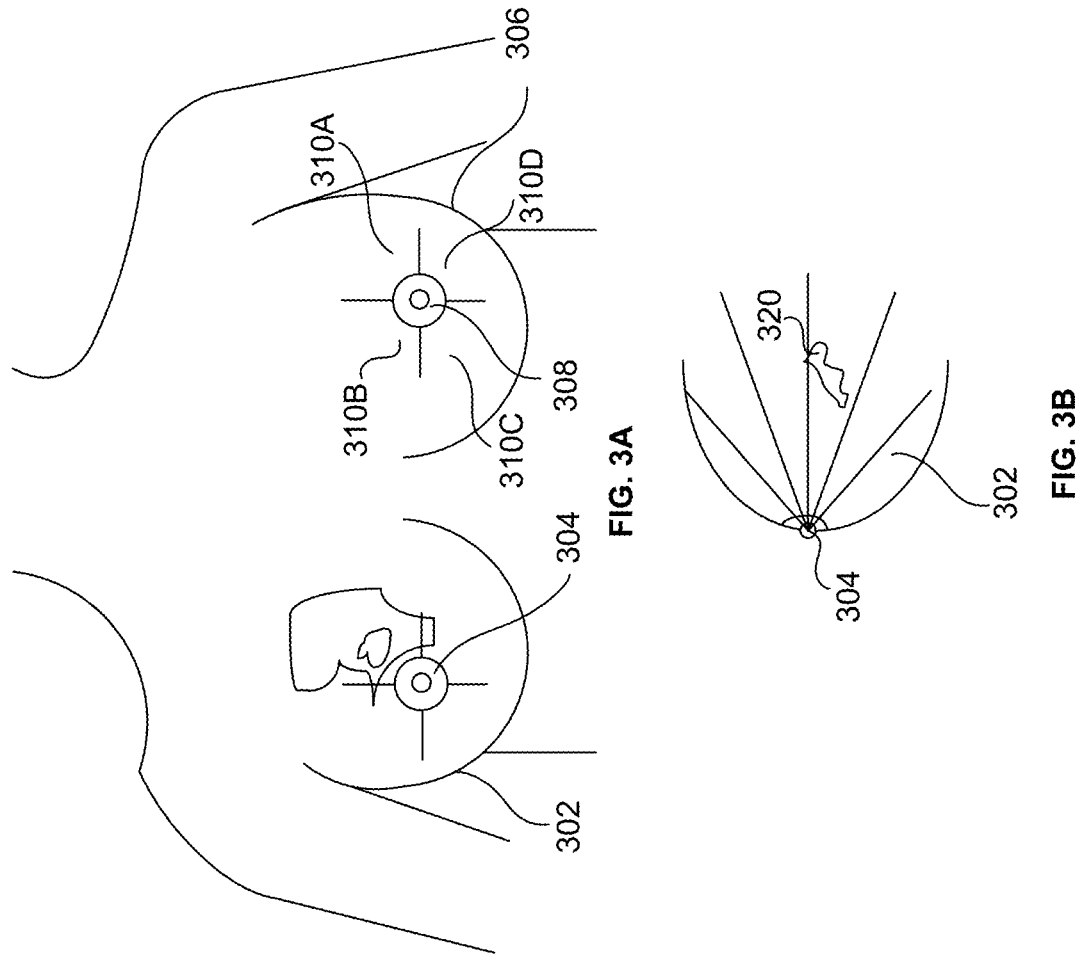
FIGS. 3A and 3B are an exemplary location of a breast lesion on a breast region of a subject according to some embodiments herein.

FIGS. 3A and 3B are an exemplary location of a breast lesion on a breast region of a subject according to some embodiments herein. The detection of breast lesion includes detection of high thermal activities on the thermal image and their corresponding location on mammography image of the subject 100. A first location being the detected hotspot region on the thermal image. The identified hotspot regions may be considered as regions corresponding to abnormalities. The thermal image of the subject's body includes a right breast 302, a right nipple point 304 which is represented as x, a left breast 306 and a left nipple point 308 which is represented as y. In some embodiments, the nipple points (x, y) (i.e. 304 and 308) are detected by the user or machine learning models. Each breast region in the thermal image includes quadrants that include at least one of (i) an upper outer quadrant (UOQ) 310A, (ii) an upper inner quadrant (UIQ) 310B, (iii) a lower inner quadrant (LIQ) 310C or (iv) a lower outer quadrant (LOQ) 310D. FIG. 3B shows the exemplary mammography image with a high-density region 320 corresponding to the high thermal activity.

Figure 4:
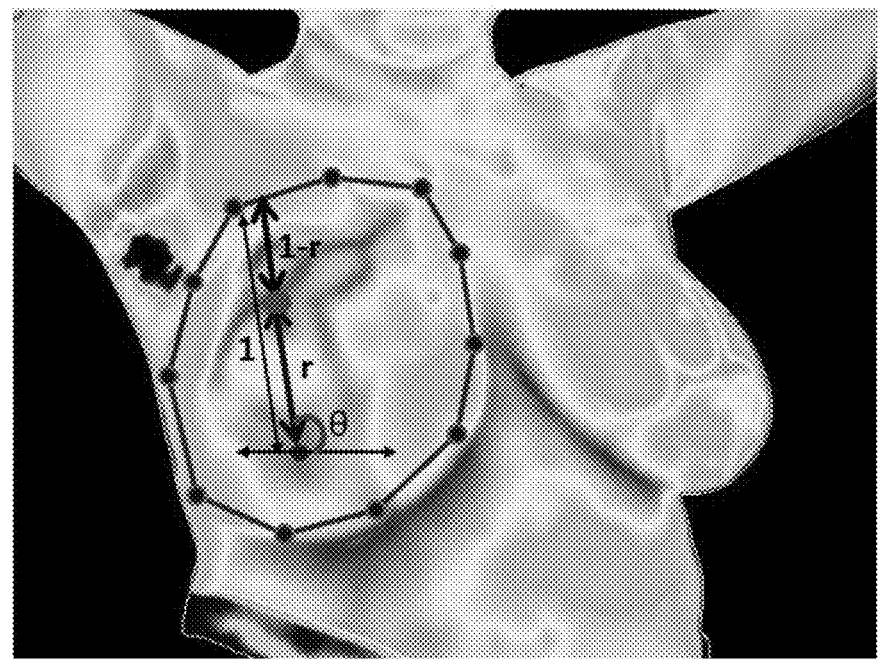
FIG. 4 illustrates an exemplary view of a location of a high temperature region determined using a nipple point as an origin and a breast region as the boundary according to an embodiment herein.

FIG. 4 illustrates an exemplary view of the location of a high temperature region determined using a nipple point as an origin and a breast region as the boundary according to an embodiment herein. In FIG. 4, the location (l) of pixels associated with high-temperature region obtained by considering a two-dimensional coordinate system is shown. In some embodiments, the first location (l) is represented using the clock position as an angle ($\theta$) and a radial distance (r). In some embodiments, location (l) is represented as zones of the breast, and distance (r) and clock position ($\theta$) are derived from the zones. In some embodiments, the location (l) of a high-temperature region on the thermography image is calculated by estimating the distance (r) and the angle ($\theta$) using the nipple point as a reference origin point of the co-ordinate system. In some embodiments, the clock position ($\theta$) is identified by detecting the angle formed by the nipple point and a centroid of the high-temperature region with a horizontal axis. In some embodiments, the clock position available as angle ($\theta$) that is represented as the corresponding degree of a clock ('o clock) of that high temperature region. In some embodiments, the clock position is available as angle ($\theta$) that is represented as a corresponding quadrant of the breasts which contains the high temperature region. In some embodiments, the distance (r) is identified by taking the ratio of the distance of the nipple point and the centroid of high temperature region to the width of the breast region.

Figure 5A:
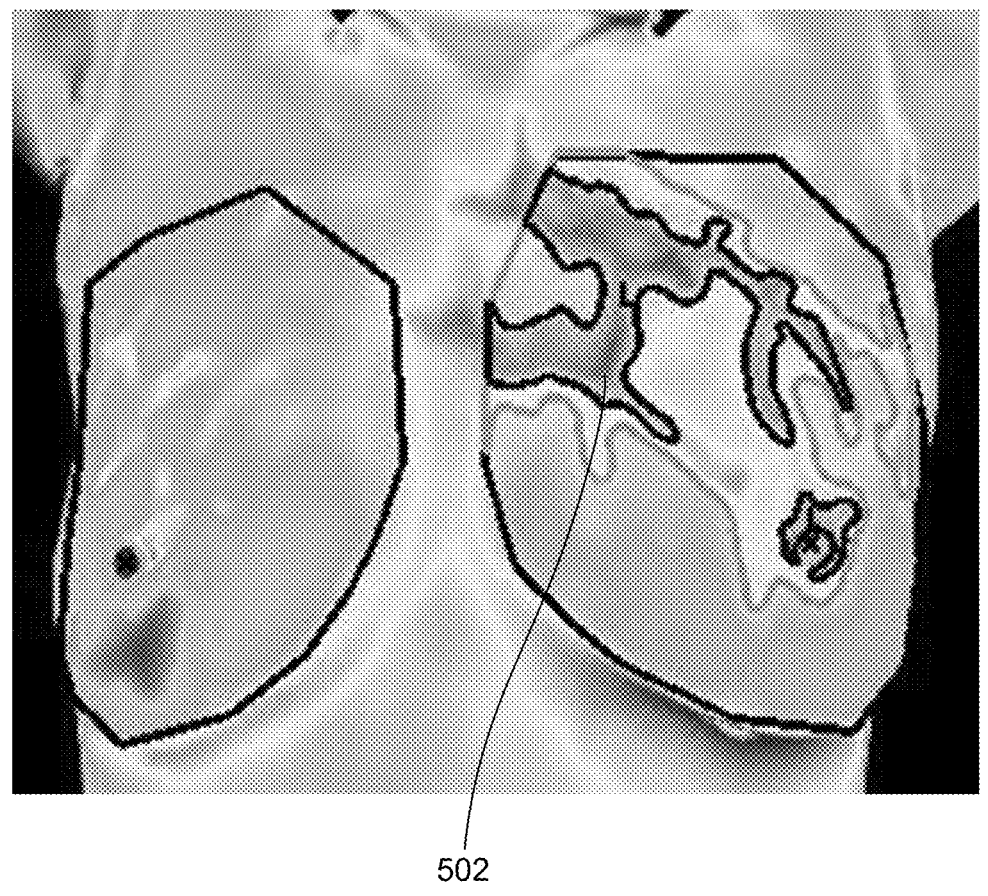
FIGS. 5A to 5B illustrate exemplary views of the high temperature region associated with a breast lesion that is identified on a breast region of the subject according to an embodiment herein.
Figure 5B:
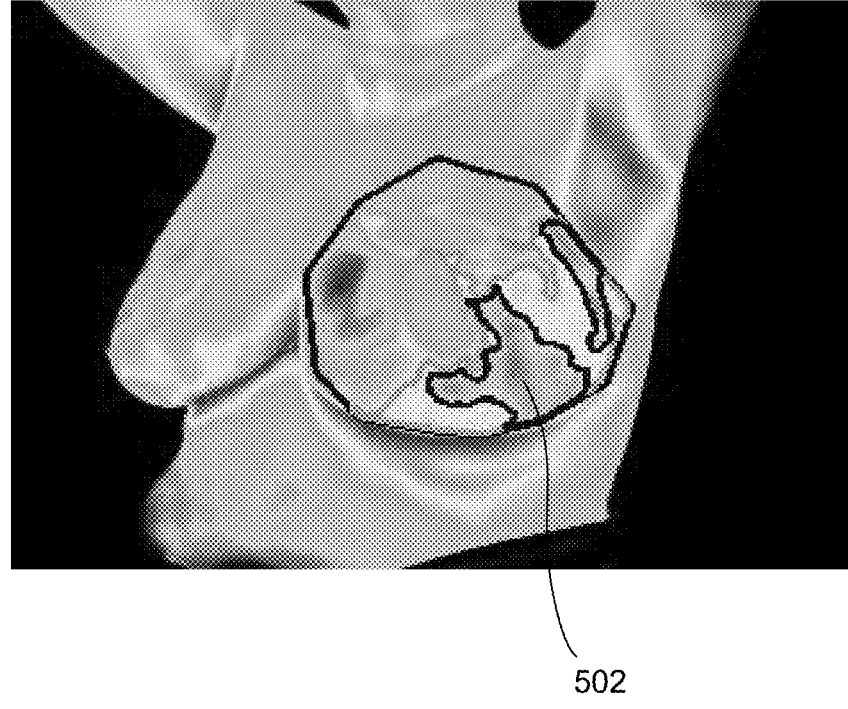

FIGS. 5A to 5B illustrate exemplary views of the high temperature region associated with a breast lesion that is identified on a breast region of the subject according to an embodiment herein. In some embodiments, a plurality of high temperature regions on the thermal image of the subject 100 as an input from the user. A high temperature region 502 is a region with high thermal activity. The computing system 104 detects the location of the high temperature region 502 corresponding to the high thermal activity. The breast region may be identified manually or via machine learning techniques. In some embodiments, a polygon ring may be marked and adjusted manually or via machine learning techniques for identification of breast region.

Figure 6A:
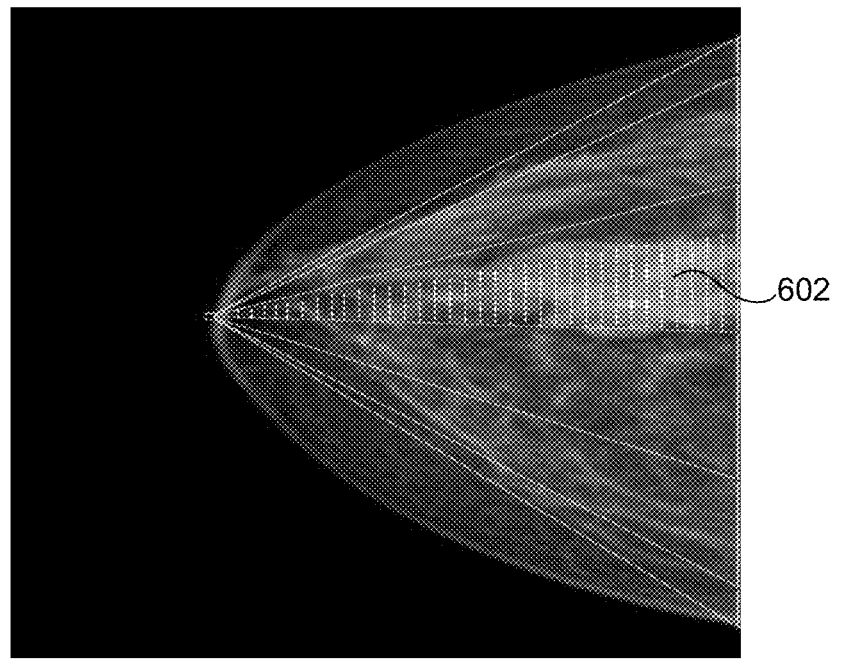
FIGS. 6A and 6B illustrate exemplary views of dividing the mammography image into different sectors using different clock positions according to an embodiment herein.
Figure 6B:
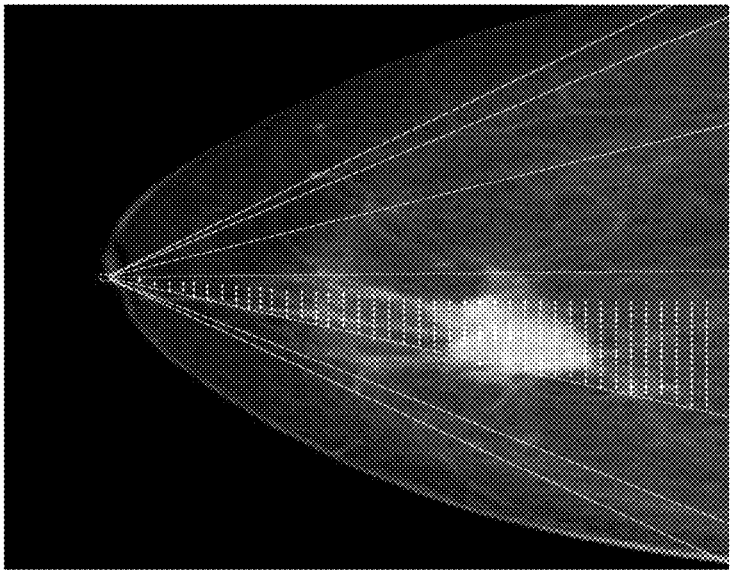

FIGS. 6A and 6B illustrate exemplary views of dividing the mammography image into different sectors using different clock positions according to an embodiment herein. The mammography image is divided into different sectors 602 corresponding to different possible clock positions. In some embodiments, the sectors correspond to quadrants of each mammography image which are identified by using the nipple point as a center of a reference coordinate system with pectoral muscle as y-axis and normal vector of pectoral muscle passing through nipple point as x-axis. In some embodiments, the sectors correspond to different zones of the breast region.

Figure 7A:
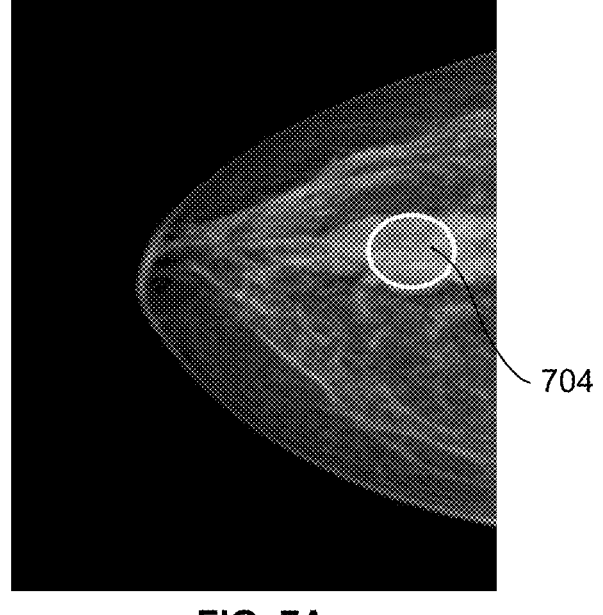
FIGS. 7A to 7C illustrate exemplary views of an annotation of the block of pixels on a mammography image corresponding to high temperature region on a thermal image according to an embodiment herein.
Figure 7B:
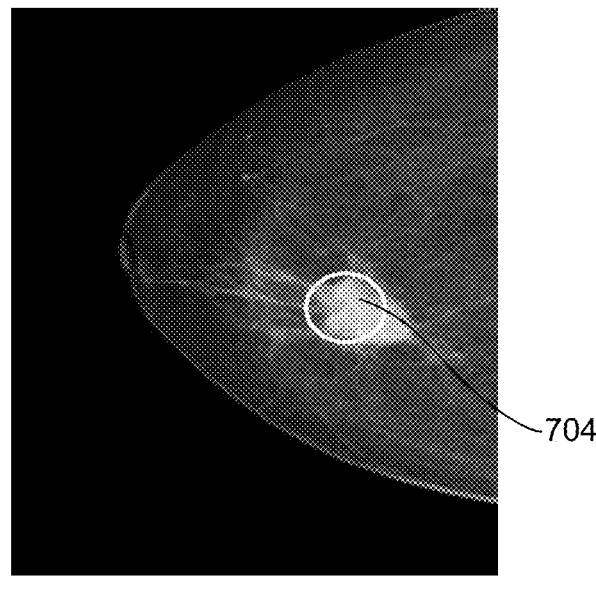
Figure 7C:
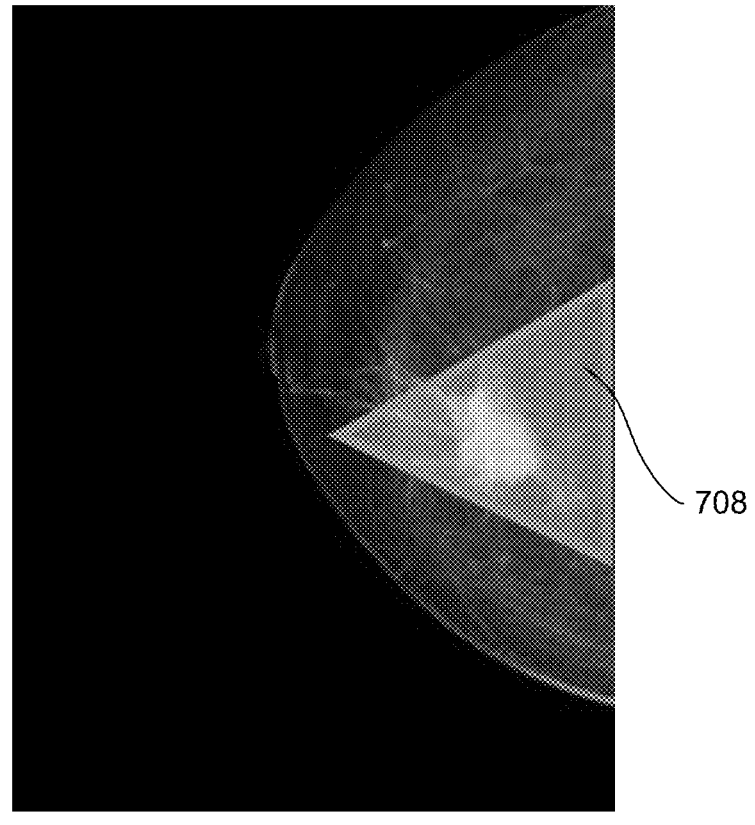

FIGS. 7A to 7C illustrate exemplary views of an annotation block of pixels on a mammography image corresponding to high temperature region on a thermal image according to an embodiment herein. In some embodiments, the mammography image is first divided into equal sectors corresponding to different clock positions. A search space representing the block of pixels ($P_m$) is identified by selecting the sector corresponding to clock position ($\theta$) and using distance (r) from the nipple region in the mammography image on this sector as one of the reference point. FIGS. 7A and 7B show the block of pixels ($P_m$) as the high-density regions in the mammography image 704 using the location (l) obtained from thermal image. FIG. 7C shows the block of pixels ($P_m$) as a triangular search region 708 with one of the vertices or reference point lying within the sector corresponding to the clock position ($\theta$) and at a distance (r) from the nipple region on the mammography image.

Figure 7D:
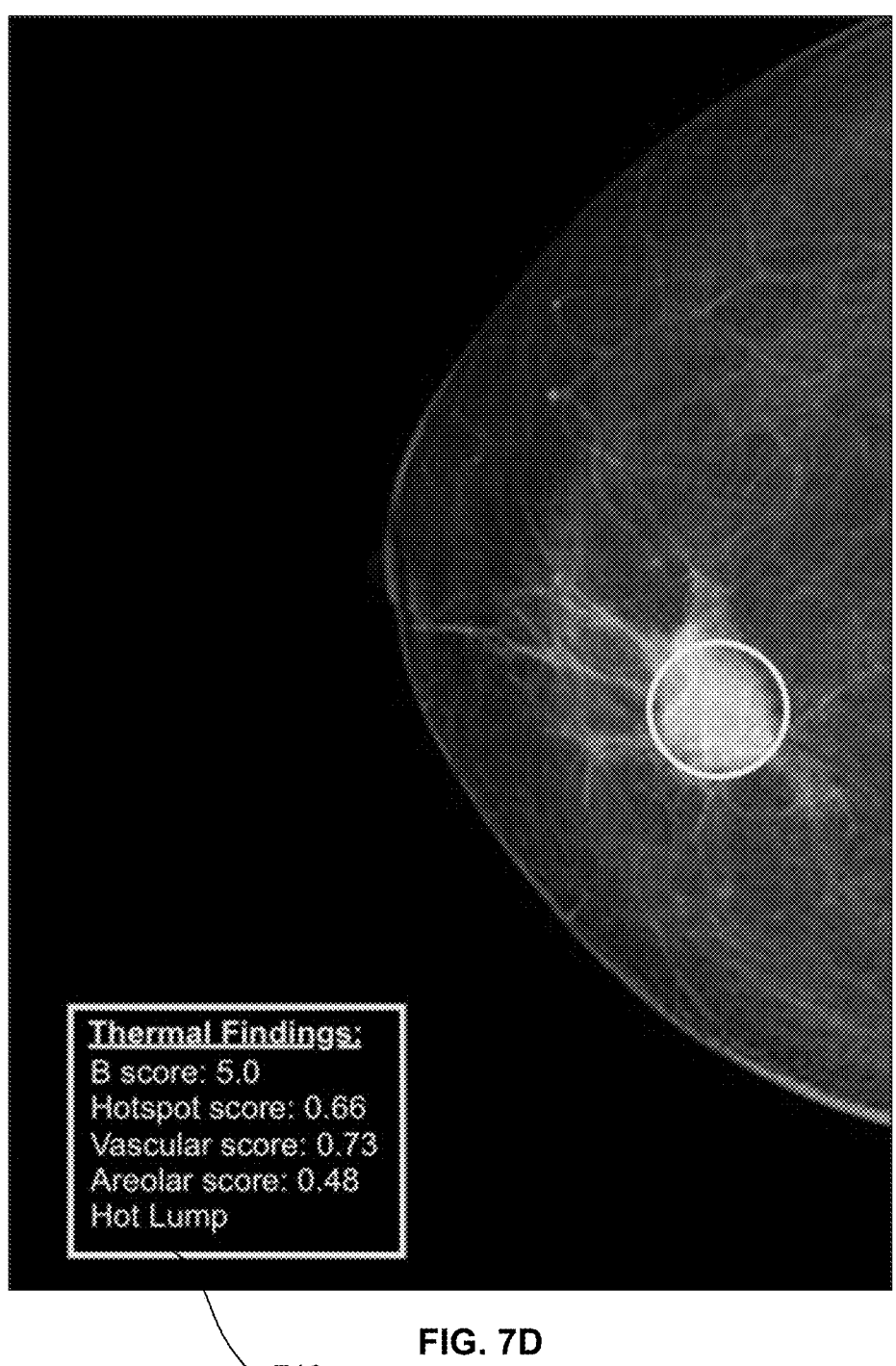
FIG. 7D illustrates an exemplary mammography image with a text annotation of the high temperature region according to an embodiment herein.

FIG. 7D illustrates an exemplary mammography image with a text annotation of the high temperature region according to an embodiment herein. The mammogram images consist of annotation that represents a block of pixels ($P_m$) corresponding to the location (l) of the block of pixels ($P_t$). In an embodiment, the mammogram image displays at least one of: (i) an annotated mammography image with markings of the determined block of pixels ($P_m$) in a different color as annotations on the mammography image or (ii) annotated mammography image with markings of the boundary of the determined block of pixels ($P_m$) in a different color as annotations on the mammography image (iii) a text report that comprises quantitative parameters of the block of pixels ($P_m$) on the mammography image corresponding to the high temperature region on the thermal image. FIG. 7D shows the annotation of the block of pixels ($P_m$) on the mammogram image corresponding to the high temperature region on the thermal image and a text annotation 710 that includes quantitative parameters of the block of pixels ($P_m$).

Figure 8A:
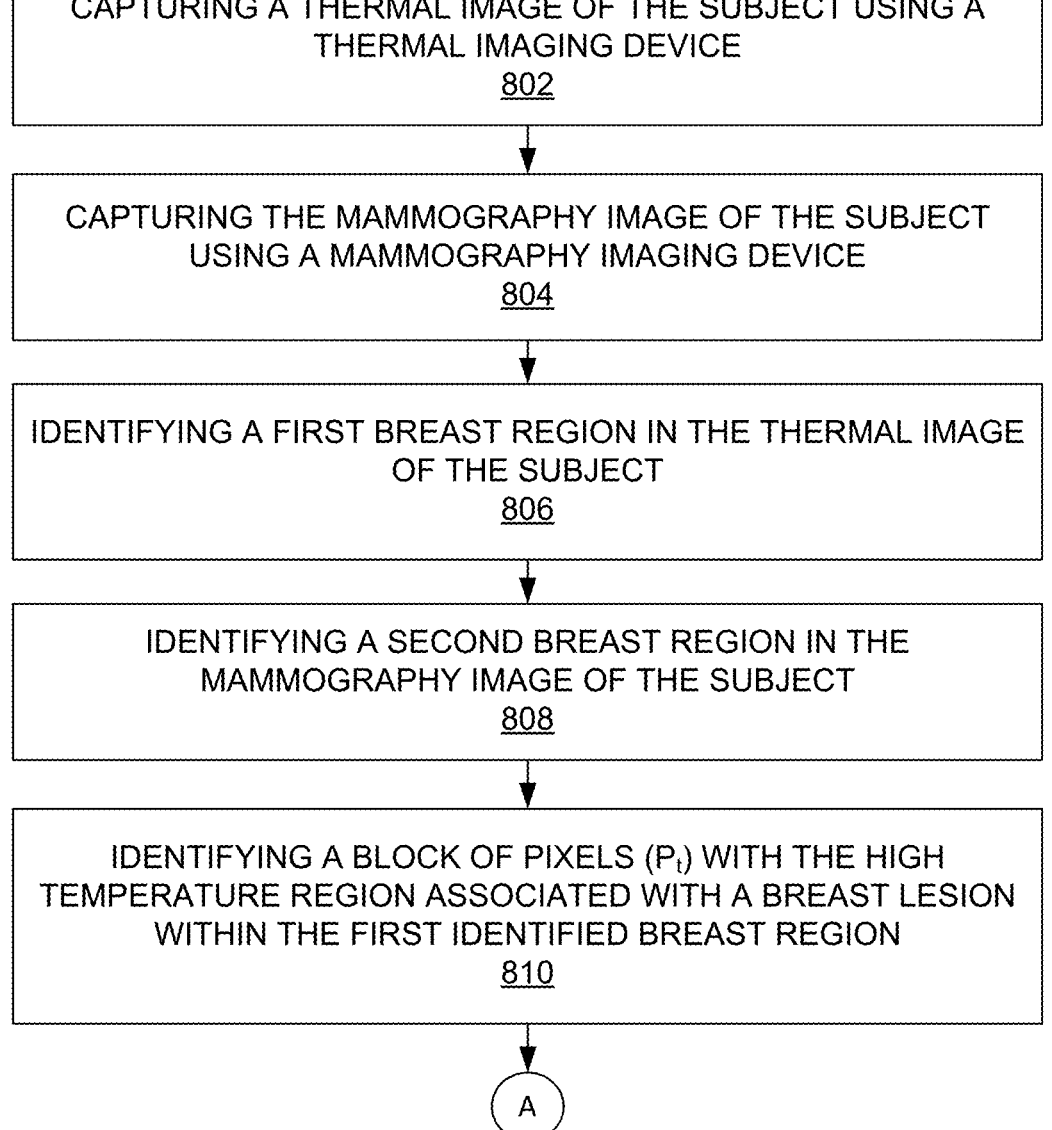

FIGS. 8A and 8B are flow diagrams that illustrate a method for annotating mammography images of a subject using thermal images and mammography images of the subject by determining a block of pixels on the mammography images corresponding to high temperature regions on the thermal images according to an embodiment herein. At step 802, a thermal image of the subject is captured using a thermal imaging device 101. At step 804, the mammography image of the subject is captured using the mammography imaging device 106. At step 806, a first breast region in the thermal image of the subject is identified. At step 808, a second breast region in the mammography image of the subject is identified. At step 810, a block of pixels ($P_t$) with the high temperature region associated with a breast lesion within the first identified breast region is identified. At step 812, a location (l) of the breast lesion corresponding to the identified block of pixels ($P_t$) is estimated. At step 814, a block of pixels ($P_m$) corresponding to the location (l) of the block of pixels ($P_t$) within the second breast region is determined on the mammography image using a first machine learning model. At step 816, a report is generated with an annotated mammography image with a marking of a determined block of pixels ($P_m$) on the mammography image of the subject corresponding to the block of pixels ($P_t$) associated with the high temperature regions on the thermal image to enable lesion identification on the mammography image of the subject.

Figure 9:
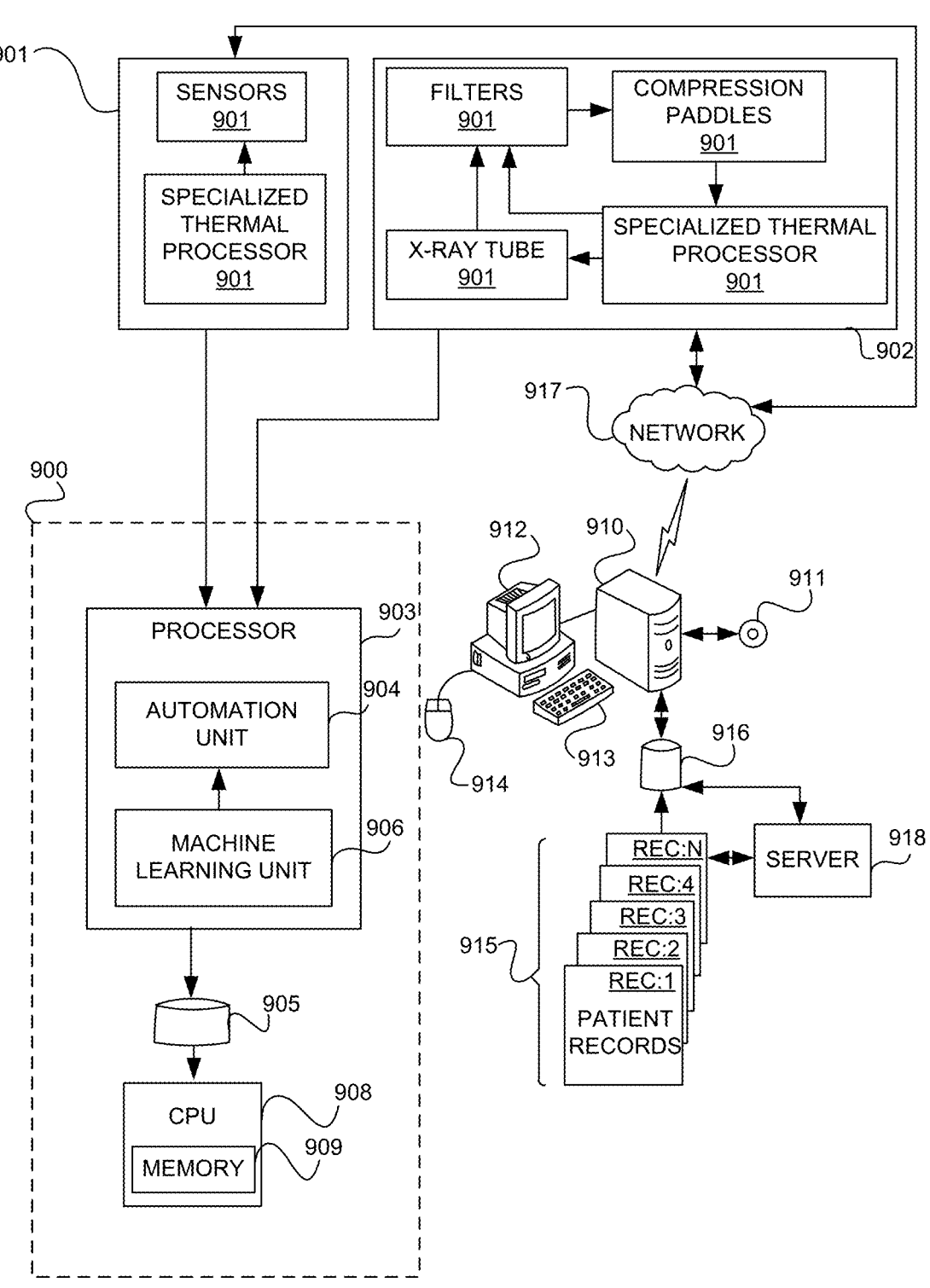
FIG. 9 illustrates a block diagram of one example system for determining a block of pixels on the mammography images corresponding to high temperature regions on the thermal images using thermal images and mammography images in accordance with the embodiments described with respect to the flow diagram of FIG. 8 according to some embodiments herein.

FIG. 9 illustrates a block diagram of one example system for determining a block of pixels on the mammography images corresponding to high temperature regions on the thermal images using thermal images and mammography images in accordance with the embodiments described with respect to the flow diagram of FIGS. 8A and 8B according to some embodiments herein. Thermal imaging device 901 captures thermal images of the subject 100. Mammography imaging device 902 captures mammography images of the subject 100. In some embodiments, the thermal imaging device 901 and the mammography imaging device 902 may transmit a thermal image or mammography image, respectively. In some embodiments, the thermal imaging device may capture a video of the subject 100. Thermal imaging device 901 consists an array of sensors that converts infrared energy into electrical signals on a per-pixel basis, wherein the array of sensors detects temperature values from the subject. The Mammography imaging device 902 converts cross section density information into pixels to generate a mammography image. Intensity values of the pixels correspond to the obtained cross section density information on a per-pixel basis. System 900 includes a processor 903 that receives the thermal image and the mammography image of the subject 100 from the thermal imaging device 901 and the mammography imaging device 902. The processor includes an automation module 904 and a machine learning unit 906. In some embodiments, the machine learning unit 906 includes at least one of a first machine learning model for determining a block of pixels ($P_m$), a second machine learning model for identifying a block of pixels ($P_t$) and a third machine learning model for identifying high-density regions on the mammography image. The automation module 904 determines the block of pixels ($P_m$) on the mammography image corresponding to the location (l) of the block of pixels ($P_t$) within the second breast region using the machine learning unit 906. In some embodiments, the block of pixels ($P_t$) with the high temperature regions are identified on the thermal image of the breast region of the subject by determining a first pixel region ($m_1$) with a temperature $T_{pixel}$, where $T_2 \leq T_{pixel} \leq T_1$, wherein $T_1$, and $T_2$ are temperature thresholds obtained from a temperature distribution. The block of pixels ($P_t$) with the high temperature regions is identified on the thermal image of the breast region of the subject by (i) determining the first pixel region ($m_1$) with a temperature $T^1_{pixel}$, where $T_2 \leq T^1_{pixel} \leq T_1$, (ii) determining a second pixel region ($m_2$) with a temperature $T^2_{pixel}$, where $T_3 \leq T^2_{pixel}$ and (iii) detecting a plurality of hotspot regions using the first pixel region ($m_1$) and the second pixel region ($m_2$) with AND or OR rules. The $T_1$, $T_2$ and $T_3$ are temperature thresholds obtained from a temperature distribution. The block of pixels ($P_t$) with the high temperature regions are identified on the first breast region of the subject using the machine learning unit 906. The automation unit 904 estimates a location (l) of the breast lesion corresponding to the identified block of pixels ($P_t$) using machine learning unit 906. In some embodiments, the plurality of high temperature regions on the breast region of the subject is obtained as an input from a user to estimate the location (l) of the breast lesion corresponding to the block of pixels ($P_t$) in the thermal image of the subject 100. The processor 903 and the automation module 904 store their results to storage device 905. The machine learning unit 906 stores and retrieves the results from storage device 905. In some embodiments, the machine learning unit 906 is used to annotate mammography images of the subject 100 using thermal images and mammography images of the subject 100 by determining a block of pixels on the mammography images corresponding to high temperature regions on the thermal images. The automation module 904 determines the_block of pixels ($P_m$) on the mammography image corresponding to the location (l) of the block of pixels ($P_t$) within the second breast region using the machine learning unit 906. Central Processing Unit 908 retrieves machine-readable program instructions from a memory 910 and is provided to facilitate the functionality of any of the modules of the system 900. CPU 908, operating alone or in conjunction with other processors, may be configured to assist or otherwise perform the functionality of any of the modules or processing units of the system 900 as well as facilitate communication between the system 900 and the workstation 911.

System 900 is shown as having been placed in communication with a workstation 910. A computer case of the workstation houses various components such as a motherboard with a processor and memory, a network card, a video card, a hard drive capable of reading/writing to machine-readable media 911 such as a floppy disk, optical disk, CD-ROM, DVD, magnetic tape, and the like, and other software and hardware needed to perform the functionality of a computer workstation. The workstation 910 further includes a display device 912, such as a CRT, LCD, or touch screen device, for displaying information, images, view angles, and the like. A user can view any of that information and make a selection from menu options displayed thereon. Keyboard 913 and mouse 914 affect a user input. It should be appreciated that the workstation 910 has an operating system and other specialized software configured to display alphanumeric values, menus, scroll bars, dials, slideable bars, pull-down options, selectable buttons, and the like, for entering, selecting, modifying, and accepting information needed for processing in accordance with the teachings hereof. The workstation 910 is further enabled to display thermal images, mammography images and the like as they are derived. A user or technician may use the user interface of the workstation 910 to set parameters and adjust various aspects of the first breast region, the second breast region, the location estimation, the block of pixels ($P_m$) and ($P_t$) and the report generation is performed, as needed or as desired, depending on the implementation. Any of these selections or inputs may be stored/retrieved to storage device 911. Default settings can be retrieved from the storage device. A user of the workstation 910 is also able to view or manipulate any of the data in the patient records, collectively at 915, stored in database 916. Server 918 is connected with 916 and 915 to access the any of the data in the patient records that are collectively at 915, and 916. In some embodiments, the server 918 is a PACS (picture archiving and communication system) server. Any of the received images, results, determined view angle, and the like, may be stored on a storage device internal to the workstation 910. Although shown as a desktop computer, the workstation 910 can be a laptop, mainframe, or a special purpose computer such as an ASIC, circuit, or the like.

Any of the components of the workstation 910 may be placed in communication with any of the modules and processing units of system 900. Any of the modules of the system 900 can be placed in communication with storage devices 905, 916 and 906 and/or computer-readable media 911 and may store/retrieve therefrom data, variables, records, parameters, functions, and/or machine-readable/executable program instructions, as needed to perform their intended functions. Each of the modules of the system 900 may be placed in communication with one or more remote devices over network 917. It should be appreciated that some or all of the functionality performed by any of the modules or processing units of the system 900 can be performed, in whole or in part, by the workstation 910. The embodiment shown is illustrative and should not be viewed as limiting the scope of the appended claims strictly to that configuration. Various modules may designate one or more components which may, in turn, comprise software and/or hardware designed to perform the intended function.

The foregoing description of the specific embodiments will so fully reveal the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments herein have been described in terms of preferred embodiments, those skilled in the art will recognize that the embodiments herein can be practiced with modification within the spirit and scope.

What is claimed is:

1. A system for annotating mammography images of a subject using thermal images and mammography images of the subject by determining a block of pixels on the mammography images corresponding to high temperature regions on the thermal images of the subject, the system comprising:

a thermal imaging device that captures a thermal image of the subject;

a mammography imaging device that captures the mammography image of the subject; and a processor that is configured to:

characterized in that, identify a first breast region in the thermal image of the subject;

identify a second breast region in the mammography image of the subject;

identify a block of pixels $(P_t)$ with the high temperature region associated with a breast lesion within the first identified breast region;

estimate a location (l) of the breast lesion corresponding to the identified block of pixels $(P_t)$;

determine, using a first machine learning model, a block of pixels $(P_m)$ on the mammography image corresponding to the location (l) of the block of pixels $(P_t)$ within the second breast region; and generate a report with an annotated mammography image with a marking of a determined block of pixels $(P_m)$ on the mammography image of the subject corresponding to the block of pixels $(P_t)$ associated with the high temperature regions on the thermal image to enable lesion identification on the mammography image of the subject.

2. The system of claim 1, wherein the thermal imaging device comprises an array of sensors that converts infrared energy into electrical signals on a per-pixel basis, wherein the array of sensors detects temperature values from the subject; and a specialized thermal processor that processes detected temperature values into pixels of a thermal image, wherein intensity values of the pixels correspond to the detected temperature values.

3. The system of claim 1, wherein the mammography imaging device comprises an X-ray tube that produces low energy X-rays;

a plurality of filters that are placed in a path of X-ray beam to modify an X-ray spectrum that is projected on a body of the subject;

a plurality of compression paddles that is attached to the body of the subject to compress a part of the body of the subject being exposed to the X-rays to obtain cross section density information; and a specialized mammogram processor that converts obtained cross section density information into pixels to generate a mammography image, wherein intensity values of the pixels correspond to the obtained cross section density information at per-pixel basis.

4. The system of claim 1, wherein the processor is configured to identify the block of pixels $(P_t)$ with high temperature regions on the thermal image of the breast region of the subject by determining a first pixel region $(m_1)$ with a temperature $T_{pixel}$, where $T_2 \leq T_{pixel} \leq T_1$, wherein $T_1$, and $T_2$ are temperature thresholds obtained from the temperature distribution of the thermal image of the subject.

5. The system of claim 1, wherein the processor is configured to identify the block of pixels $(P_t)$ with the high temperature regions on the thermal image of the breast region of the subject by:

determining the first pixel region $(m_1)$ with a temperature $T^1_{pixel}$, where $T_2 \leq T^1_{pixel} \leq T_1$;

determining a second pixel region $(m_2)$ with a temperature $T^2_{pixel}$, where $T_3 \leq T^2_{pixel}$; and detecting a plurality of hotspot regions using the first pixel region $(m_1)$ and the second pixel region $(m_2)$ with AND or OR rules, wherein $T_1$, $T_2$ and $T_3$ are temperature thresholds obtained from the temperature distribution of the thermal image of the subject.

6. The system of claim 1, wherein the processor is configured to obtain the plurality of high temperature regions on the first breast region of the subject as an input from the user to estimate the location (l) of the breast lesion corresponding to the block of pixels $(P_t)$ in the thermal image of the subject.

7. The system of claim 1, wherein the processor is configured to identify block of pixels $(P_t)$ with high temperature regions on the first breast region of the subject using a second machine learning model, wherein the second machine learning model is trained by providing a plurality of thermal images and corresponding annotated high temperature regions associated with different patients as training data.

8. The system of claim 1, wherein the first machine learning model identifies the block of pixels $(P_m)$ on the mammography image corresponding to the location (l) on the thermography image by:

obtaining a breast quadrant corresponding to the location (l);

identifying a view of the mammography image;

dividing the mammography image into different quadrants; and identifying the block of pixels $(P_m)$ that lie within a obtained quadrant corresponding to location (l) of the breast lesion on the thermographic image.

9. The system (104) of claim 1, wherein the first machine learning model identifies the block of pixels $(P_m)$ on the mammography image corresponding to the location (l) on the thermography image by:

identify candidate block of pixels with high density in the mammography image;

obtaining a nipple point (N) on the mammography image;

calculating locations ($lm_{1-n}$) of each candidate block of pixels with respect to a obtained nipple point (N);

comparing the locations ($lm_{1-n}$) of each of the candidate block of pixels with the location (l) of the breast lesion on the thermographic image; and selecting the block of pixels ($P_m$) among the candidate block of pixels by selecting a block of pixels corresponding to a nearest location ($lm_i$) among the locations ($lm_{1-n}$) that is close to the location (l) of the breast lesion on the thermographic image.

10. The system of claim 9, wherein the processor is configured to identify the block of pixels ($P_m$) as the high-density regions in the mammography image within the sector corresponding to the clock position (θ) and distance (r) from the nipple region in the mammography image.

11. The system of claim 1, wherein the first machine learning model identifies the block of pixels ($P_m$) on the mammography image corresponding to the location (l) on the thermography image comprises:

obtaining a clock position (θ) and a distance (r) corresponding to the location (l);

dividing the mammography image into different sectors corresponding to different clock positions; and identifying the block of pixels ($P_m$) that lie within the sector corresponding to the clock position (θ) and distance (r) from the nipple region in the mammography image.

12. The system of claim 11, wherein the processor is configured to identify the high-density regions on the mammography image of the subject using a third machine learning model, wherein the third machine learning model is trained by providing a plurality of mammography images and the corresponding annotated high-density lesions associated with different patients as training data.

13. The system of claim 12, wherein the markings comprise an annotation of the block of pixels ($P_m$) on the mammogram image corresponding to the high temperature region on the thermal image and a text annotation that comprises quantitative parameters of the block of pixels ($P_m$).

14. The system of claim 1, wherein the report comprises at least one of annotated mammography image with markings of the determined block of pixels ($P_m$) in a different color as annotations on the mammography image;

annotated mammography image with markings of the boundary of the determined block of pixels ($P_m$) in a different color as annotations on the mammography image;

a text report that comprises quantitative parameters of the block of pixels ($P_m$) on the mammography image corresponding to the high temperature region on the thermal image.

15. A method for annotating mammography images of a subject using thermal images and mammography images of the subject by determining a block of pixels on the mammography images corresponding to high temperature regions on the thermal images of the subject comprising, capturing a thermal image of the subject using a thermal imaging device;

capturing the mammography image of the subject using a mammography imaging device;

identifying a first breast region in the thermal image of the subject;

identifying a second breast region in the mammography image of the subject;

identifying a block of pixels ($P_t$) with the high temperature region associated with a breast lesion within the first identified breast region;

estimating a location (l) of the breast lesion corresponding to the identified block of pixels ($P_t$);

determining, using a first machine learning model, a block of pixels ($P_m$) on the mammography image corresponding to the location (l) of the block of pixels ($P_t$) within the second breast region; and generating a report with an annotated mammography image with a marking of a determined block of pixels ($P_m$) on the mammography image of the subject corresponding to the block of pixels ($P_t$) associated with the high temperature regions on the thermal image to enable lesion identification on the mammography image of the subject.

16. The method of claim 15, further comprises identifying the block of pixels ($P_t$) with high temperature regions on the thermal image of the breast region of the subject by determining a first pixel region ($m_1$) with a temperature $T_{pixel}$, where $T_2 \leq T_{pixel} \leq T_1$, wherein $T_1$, and $T_2$ are temperature thresholds obtained from the temperature distribution of the thermal image of the subject.

17. The method of claim 15, further comprises identifying the block of pixels ($P_m$) on the mammography image corresponding to the location (l) on the thermography image by:

obtaining a breast quadrant corresponding to the location (l);

identifying a view of the mammography image;

dividing the mammography image into different quadrants; and identifying the block of pixels ($P_m$) that lie within a obtained quadrant corresponding to location (l) of the breast lesion on the thermographic image.

18. The method of claim 15, wherein the first machine learning model identifies the block of pixels ($P_m$) on the mammography image corresponding to the location (l) on the thermography image by:

identify candidate block of pixels with high density in the mammography image;

obtaining a nipple point (N) on the mammography image;

calculating locations ($lm_{1-n}$) of each candidate block of pixels with respect to a obtained nipple point (N);

comparing the locations ($lm_{1-n}$) of each of the candidate block of pixels with the location (l) of the breast lesion on the thermographic image; and selecting the block of pixels ($P_m$) among the candidate block of pixels by selecting a block of pixels corresponding to a nearest location ($lm_i$) among the locations ($lm_{1-n}$) that is close to the location (l) of the breast lesion on the thermographic image.

19. The method of claim 15, wherein the first machine learning model identifies the block of pixels ($P_m$) on the mammography image corresponding to the location (l) on the thermography image comprises:

obtaining a clock position (θ) and a distance (r) corresponding to the location (l);

dividing the mammography image into different sectors corresponding to different clock positions; and identifying the block of pixels ($P_m$) that lie within the sector corresponding to the clock position (θ) and distance (r) from the nipple region in the mammography image.

20. A non-transitory computer-readable storage medium storing the one or more sequence of instructions, which when executed by one or more processors, causes to perform a method for annotating mammography images of a subject using thermal images and mammography images of the subject by determining a block of pixels on the mammography images corresponding to high temperature regions on the thermal images of the subject comprising, capturing a thermal image of the subject using a thermal imaging device;

capturing the mammography image of the subject using a mammography imaging device;

identifying a first breast region in the thermal image of the subject;

identifying a second breast region in the mammography image of the subject;

identifying a block of pixels ($P_t$) with the high temperature region associated with a breast lesion within the first identified breast region;

estimating a location (l) of the breast lesion corresponding to the identified block of pixels ($P_t$);

determining, using a first machine learning model, a block of pixels ($P_m$) on the mammography image corresponding to the location (l) of the block of pixels ($P_t$) within the second breast region; and generating a report with an annotated mammography image with a marking of a determined block of pixels ($P_m$) on the mammography image of the subject corresponding to the block of pixels ($P_t$) associated with the high temperature regions on the thermal image to enable lesion identification on the mammography image of the subject.

\* \* \* \* \*